(12) United States Patent
Doyle et al.

(10) Patent No.: US 10,451,542 B2
(45) Date of Patent: Oct. 22, 2019

(54) LOCAL PURGE WITHIN METROLOGY AND INSPECTION SYSTEMS

(71) Applicant: Nanometrics Incorporated, Milpitas, CA (US)

(72) Inventors: Paul A. Doyle, Milpitas, CA (US); Ryan Tsai, Sunnyvale, CA (US); Morgan A. Crouch, Santa Clara, CA (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

(21) Appl. No.: 15/994,958

(22) Filed: May 31, 2018

(65) Prior Publication Data

US 2019/0170634 A1 Jun. 6, 2019

Related U.S. Application Data

(60) Provisional application No. 62/595,023, filed on Dec. 5, 2017.

(51) Int. Cl.
| | |
|---|---|
| *G01N 21/15* | (2006.01) |
| *G03F 7/20* | (2006.01) |
| *G01N 21/95* | (2006.01) |
| *G03F 1/84* | (2012.01) |
| *G01N 21/956* | (2006.01) |
| *H01L 21/66* | (2006.01) |

(52) U.S. Cl.
CPC ......... *G01N 21/15* (2013.01); *G01N 21/9501* (2013.01); *G01N 21/956* (2013.01); *G03F 1/84* (2013.01); *G03F 7/7005* (2013.01); *H01L 22/12* (2013.01); *G01N 2021/151* (2013.01)

(58) Field of Classification Search
CPC ............. G01N 2021/151; G01N 21/15; G01N 21/9501; G01N 21/956; G03F 7/7005; G03F 1/84; H01L 22/12
USPC ........................ 356/445, 426–428, 932, 437, 356/237.1–237.6, 239.1–239.8
See application file for complete search history.

(56) References Cited

U.S. PATENT DOCUMENTS

| | | |
|---|---|---|
| 4,557,599 A | 12/1985 | Zimring |
| 6,413,321 B1 | 7/2002 | Kim et al. |
| 6,983,892 B2 | 1/2006 | Noorbakhsh et al. |
| 7,138,640 B1 | 11/2006 | Delgado et al. |
| 7,489,389 B2 | 2/2009 | Shibazaki |

(Continued)

OTHER PUBLICATIONS

International Search Report and Written Opinion dated May 14, 2019 from PCT/US2018/063312, filed Nov. 30, 2018.

(Continued)

*Primary Examiner* — Tri T Ton
(74) *Attorney, Agent, or Firm* — Silicon Valley Patent Group LLP

(57) ABSTRACT

A purge system includes a purge gas distribution manifold that includes at least one port through which light beam from an optical metrology or inspection head is transmitted. The purge gas distribution manifold includes a bottom surface having one or more apertures through which purge gas is expelled. The bottom surface is held in close proximity to the top surface of the substrate and the apertures may be distributed over the bottom surface of the purge gas distribution manifold so that purge gas is uniformly distributed over the entirety of the top surface of the substrate at all measurement positions of the substrate with respect to the optical metrology or inspection head.

12 Claims, 7 Drawing Sheets

(56) References Cited

U.S. PATENT DOCUMENTS

| | | |
|---|---|---|
| 7,542,127 B2 | 6/2009 | Sengers et al. |
| 7,755,764 B2 | 7/2010 | Kwak et al. |
| 7,981,472 B2 | 7/2011 | Dalton et al. |
| 8,817,250 B2 | 8/2014 | Doyle et al. |
| 8,830,486 B2 | 9/2014 | Kwak et al. |
| 9,257,320 B2 | 2/2016 | Fosnight et al. |
| 2006/0021568 A1 | 2/2006 | Matsumoto |
| 2010/0024887 A1 | 2/2010 | Williams et al. |
| 2012/0052216 A1 | 3/2012 | Hanawa et al. |
| 2012/0321786 A1 | 12/2012 | Satitpunwaycha et al. |
| 2014/0085618 A1 | 3/2014 | Delgado et al. |

OTHER PUBLICATIONS

Invitation to Pay Additional Fees dated Mar. 21, 2019 from PCT/US2018/063312, filed Nov. 30, 2018.

LOCAL PURGE WITHIN METROLOGY AND INSPECTION SYSTEMS

CROSS REFERENCE TO RELATED APPLICATIONS

This application claims benefit to and priority under 35 USC § 119 to U.S. Provisional Application No. 62/595,023, entitled "LOCAL PURGE WITHIN METROLOGY AND INSPECTION SYSTEMS," filed Dec. 5, 2017, which is incorporated herein by reference in its entirety.

FIELD OF THE INVENTION

The present invention is related to optical metrology and inspection systems, and in particular to a localized purging of optical metrology and inspection systems.

BACKGROUND

To improve process control for some semiconductor manufacturing processes, optical metrology and substrate inspection systems are used to measure and quickly provide feedback for real-time control of the processes. Metrology and substrate inspection processes in semiconductor manufacturing, however, are vulnerable to Airborne Molecular Contamination (AMC) as well as moisture within the environment. Additionally, the substrates themselves are also vulnerable to AMC and moisture in the environment, which may produce contaminants on the surface of a substrate or form film growth or corrosion/oxidation. Moreover, the use of AMC filtration may reduce film growth rate, but does not address humidity control effectively enough to prevent corrosion/oxidation.

Purge systems are sometimes used to protect the metrology and substrate inspection systems and/or substrates under test. By way of example, purge systems sometimes use a purged chamber into which a purge gas or clean dry air is provided. Use of purged chamber, however, requires near vacuum chamber sealing integrity to the atmosphere, and significant safety controls to protect service personnel from asphyxiation hazards. Moreover, a significant amount of purge gas or air may be required to adequately purge a chamber. Other purge systems provide a purge gas or air to the beam path of the optical metrology or inspection device. Thus, purge gas or air contacts limited areas of the substrate during testing, but the remainder of the substrate may still be exposed to the atmosphere including AMC and humidity. Accordingly, improvements over conventional purge systems are desired.

SUMMARY

A purge system includes a purge gas distribution manifold that includes at least one port through which a light beam from an optical metrology or inspection head is transmitted. The purge gas distribution manifold includes a bottom surface having one or more apertures through which purge gas is expelled. The bottom surface is held in close proximity to the top surface of the substrate and the apertures are distributed over the bottom surface of the purge gas distribution manifold so that purge gas is uniformly distributed over the entirety of the top surface of the substrate at all measurement positions of the substrate with respect to the optical metrology or inspection head.

In one implementation, an apparatus includes an optical metrology or inspection head that produces a light beam that is incident on a substrate to be optically measured and is received by the optical metrology or inspection head after interacting with the substrate, a chuck for holding the substrate, wherein at least one of the chuck and the optical metrology or inspection head is movable to position the substrate at a plurality of measurement positions with respect to the optical metrology or inspection head, a purge gas distribution manifold coupled to a purge gas source, the purge gas distribution manifold having at least one port through which the light beam is transmitted, the purge gas distribution manifold having a bottom surface that is 25 mm or less from a top surface of the substrate and has a plurality of apertures through which purge gas is expelled over the top surface of the substrate, wherein the plurality of apertures are distributed over a surface area that is at least as large as a surface area of the top surface of the substrate to distribute the purge gas over an entirety of the top surface of the substrate at all measurement positions of the substrate with respect to the optical metrology or inspection head.

In one implementation, an apparatus includes an optical metrology or inspection head that produces a light beam that is incident on a substrate to be optically measured and is received by the optical metrology or inspection head after interacting with the substrate, a chuck for holding the substrate, wherein at least one of the chuck and the optical metrology or inspection head is movable to position the substrate at a plurality of measurement positions with respect to the optical metrology or inspection head, a purge gas distribution manifold coupled to a purge gas source, the purge gas distribution manifold having at least one port through which the light beam is transmitted, wherein there is relative motion between the purge gas distribution manifold and the substrate when the at least one of the chuck and the optical metrology or inspection head is moved to position the substrate at the plurality of measurement positions with respect to the optical metrology or inspection head, the purge gas distribution manifold having a plurality of apertures through which purge gas is expelled over a top surface of the substrate, wherein the plurality of apertures are distributed over a surface area that is larger than a surface area of the top surface of the substrate to distribute the purge gas over an entirety of the top surface of the substrate at all measurement positions of the substrate with respect to the optical metrology or inspection head.

In one implementation, an apparatus includes an optical metrology or inspection head that produces a light beam that is incident on a substrate to be optically measured and is received by the optical metrology or inspection head after interacting with the substrate, a chuck for holding the substrate, wherein at least one of the chuck and the optical metrology or inspection head is movable to position the substrate at a plurality of measurement positions with respect to the optical metrology or inspection head, a purge gas distribution manifold coupled to a purge gas source, the purge gas distribution manifold having at least one port through which the light beam is transmitted, the purge gas distribution manifold is held linearly stationary with respect to the substrate when the at least one of the chuck and the optical metrology or inspection head is moved to position the substrate at the plurality of measurement positions with respect to the optical metrology or inspection head, the purge gas distribution manifold having a plurality of apertures through which purge gas is expelled, wherein a distribution area of the plurality of apertures is within 25 percent of a surface area of a top surface of the substrate to distribute the purge gas over an entirety of the top surface of the substrate at all measurement positions of the substrate with respect to the optical metrology or inspection head.

In one implementation, an apparatus includes an optical metrology or inspection head that produces a light beam that is incident on a substrate to be optically measured and is received by the optical metrology or inspection head after interacting with the substrate, a chuck for holding the substrate, wherein at least one of the chuck and the optical metrology or inspection head is movable to position the substrate at a plurality of measurement positions with respect to the optical metrology or inspection head, a ceiling having at least one port through which the light beam is transmitted, the ceiling having a bottom surface that is 25 mm or less from a top surface of the substrate; and a fence surrounding the substrate on the chuck, wherein the fence is held linearly stationary with respect to the substrate when the at least one of the chuck and the optical metrology or inspection head is moved to position the substrate at the plurality of measurement positions with respect to the optical metrology or inspection head, the fence having one or more apertures below the top surface of the substrate and through which purge gas is expelled over the top surface of the substrate to distribute the purge gas over an entirety of the top surface of the substrate at all measurement positions of the substrate with respect to the optical metrology or inspection head.

DETAILED DESCRIPTION

Figure 1:
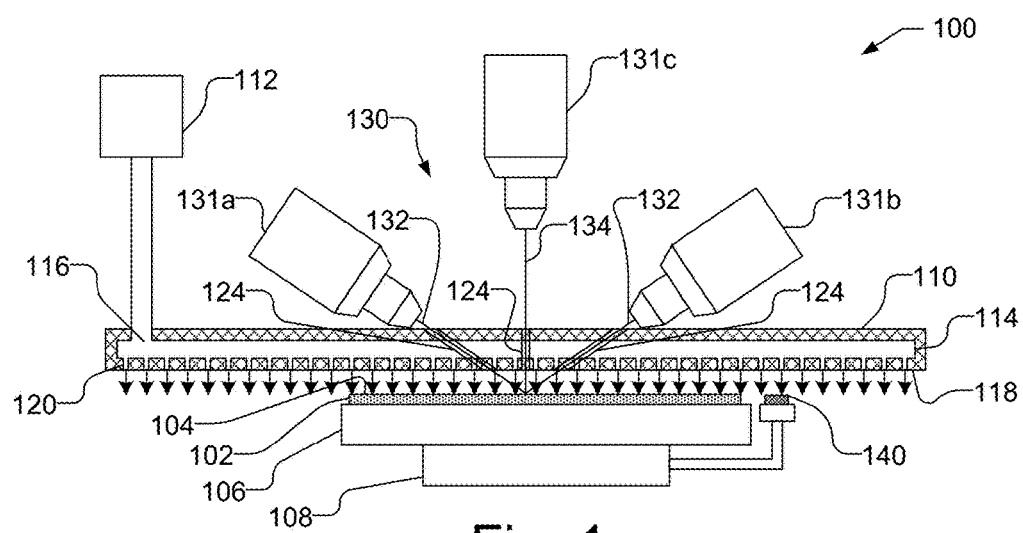
FIG. 1 illustrates a side view of a purge system with a purge gas distribution manifold that provides a localized clean environment for the top side of a substrate.

FIG. 1 illustrates a side view of a purge system 100 that provides a purged environment to the entirety of the top side of a substrate 102 being inspected or measured. The purged environment is localized to the surface of the substrate 102, as opposed to the entire environment surrounding the substrate 102 or metrology or inspection device, e.g., as in a conventional purge chamber. The purge system 100 includes a purge gas distribution manifold 110 that distributes the purge gas and is positioned so that only a small gap is between a bottom surface 118 of the purge gas distribution manifold 110 and the top surface 104 of the substrate 102. For example, the bottom surface 118 of the purge gas distribution manifold 110 may be 25 mm or less from the top surface 104 of the substrate 102. The small gap between the purge gas distribution manifold 110 and the substrate 102 minimizes the purge gas consumption while providing good shielding purity in the local environment over the substrate 102.

The purge gas distribution manifold 110 is fluidically coupled to a purge gas source 112, which may supply an inert gas, such as nitrogen or argon or air, which is purified clean dry air, a combination thereof, or any other suitable inert gas. The purge gas distribution manifold 110 includes a distribution plenum 114, which distributes the purge gas from the inlet 116 coupled to the purge gas source 112 and distributes the purge gas over a large area within the purge gas distribution manifold 110. The bottom surface 118 of the purge gas distribution manifold 110 includes a plurality of apertures 120 through which the purge gas from the distribution plenum 114 is expelled, as illustrated by the arrows.

Figures 2A, 2B:
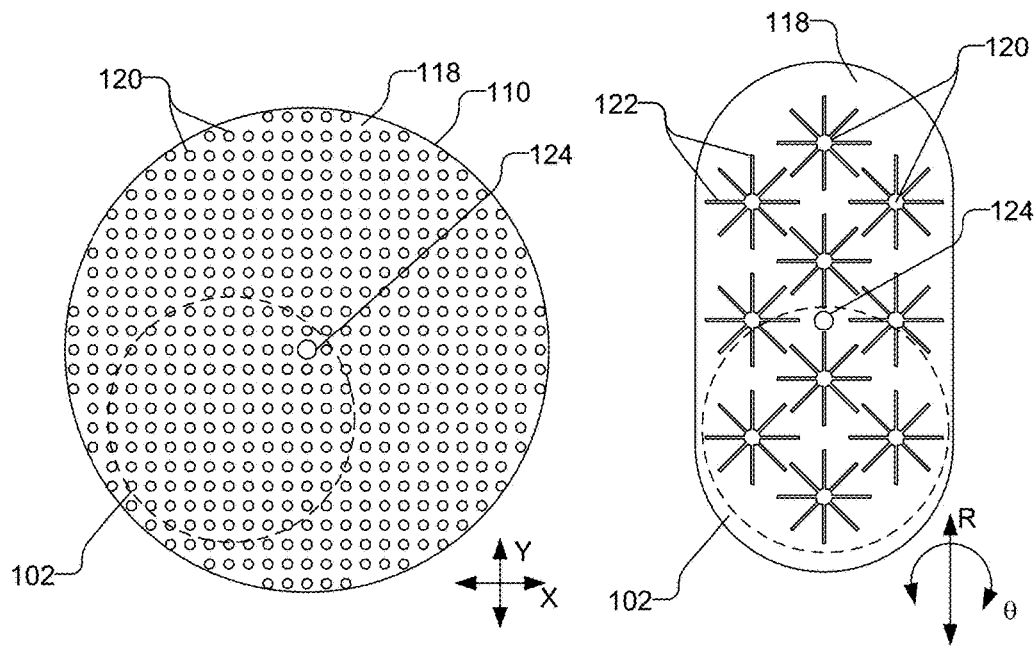
FIGS. 2A and 2B illustrate embodiments of a bottom surface of the purge gas distribution manifold.

FIGS. 2A and 2B illustrate different implementations of the bottom surface 118 of the purge gas distribution manifold 110 relative to a substrate 102. FIG. 2A illustrates an implementation of the purge gas distribution manifold 110, where the substrate is positioned for measurement using Cartesian coordinate plane (X,Y) directions and FIG. 2B illustrates an implementation where the substrate is moved in the Polar coordinate plane (R, θ). As illustrated, apertures 120 in the bottom surface may be holes uniformly or non-uniformly distributed over the area of the bottom surface 118. If desired, as illustrated in FIG. 2B, distribution grooves 122 may be coupled to the holes in the bottom surface 118 in order to assist in a uniform distribution of the purge gas. By way of example, the holes may be 10 mm or less, e.g., 2 mm, in diameter, and there may be between 1 mm to 25 mm between the holes if there are no distribution grooves. With the use of distribution grooves, which may be, e.g., 2 mm-10 mm wide, fewer holes may be required and the spacing between holes may be increased, e.g., up to 50 mm-75 mm between holes. Moreover, with distribution grooves, a greater flow rate may be desired, and thus holes with a larger diameter, e.g., 10 mm, may be used. Additionally, the size of the holes may selected as a function of position in the bottom surface 118 of purge gas distribution manifold 110 to balance the flow rates for uniform protection over the entire surface of the substrate 102. It should be understood, however, that while the general shape of the purge gas distribution manifold 110 may vary based on how the substrate moves, the specific implementation of the bottom surface of the purge gas distribution manifold 110 is not limited to movement of the substrate in any particular coordinate system.

In another implementation, the bottom surface 118 of the purge gas distribution manifold 110 or portions of the bottom surface 118 may be a porous media, such as a porous carbon or polymer, or sintered metal or polymer, where the purge gas is expelled through the apertures, i.e., pores, in the porous media. In some implementations, a porous media may be located within apertures, which may be 25 mm or less in diameter, in the bottom surface 118 to the throttle the flow of the purge gas and to provide a uniform distribution of gas over the substrate surface. The porous media, apertures and distribution grooves may be used together, or alternatively, the porous media and apertures, without distribution grooves, may be uniformly or non-uniformly distributed over the area of the bottom surface 118.

By positioning the purge gas distribution manifold 110 close to the top surface 104 of the substrate 102 and the use of the plurality of apertures 120 distributed over the bottom surface 118 of the purge gas distribution manifold 110, a uniform distribution of the purge gas over the entirety of the top surface 104 of the substrate 102 may be produced with only a modest flow rate of purge gas. By way of example, modeling has shown flow rates on the order of 1 cfm may reduce O2 levels below 0.02%, and further design optimization may yield even further reduced flow rates at similar O2 concentrations. For some applications, the flow rate may be controlled and reduced via a software recipe control, or by setting a lower flow rate passively. An exhaust port (not shown) may be provided, e.g., below the stage 108, to remove the purge gas.

As illustrated in FIG. 1, the purge system 100 is used with an optical metrology or inspection head 130 that may include one or more metrology or inspection devices. Optical metrology or inspection head 130 is illustrated as including objective lenses 131a, 131b, which produce light beam 132 that is obliquely incident on the substrate 102, and an objective lens 131c, which produces light beam 134 that is normally incident on the substrate 102. The objective lenses 131a, 131b, by way of example, may be part of an ellipsometer or other instrument that uses obliquely incident light. The light beam 132 may be emitted by objective lens 131a and received by objective lens 131b after interacting with the substrate 102. The object lens 131c, by way of example, may be a reflectometer or other instrument that uses normally incident light. The light beam 134 is emitted by objective lens 131c and received by objective lens 131c after interacting with the substrate 102. For the sake of simplicity, the optical metrology or inspection head 130 is illustrated as only objective lenses, but it should be understood that additional optical elements, such as a light source, detector, polarizing elements, etc., are included in an optical metrology or inspection device, but illustrations of these additional elements are unnecessary for understanding the operation of the purge system 100.

The purge gas distribution manifold 110 includes one or more ports 124 through which the light beams 132 and 134 from an optical metrology or inspection head 130 is transmitted to and from the substrate 102. The purge gas distribution manifold 110 may include two separate ports 124 that are slanted with respect to the bottom surface 118 to accommodate the obliquely incident light from the optical metrology or inspection head 130 and a port 124 that is perpendicular to the bottom surface 118 to accommodate the normally incident beam 134. If desired, a single large port 124 may be used with the obliquely incident light beam 132 and normally incident light beam 134 of the optical metrology or inspection head 130, but this may affect distribution of the purge gas over the substrate 102.

Figure 3:
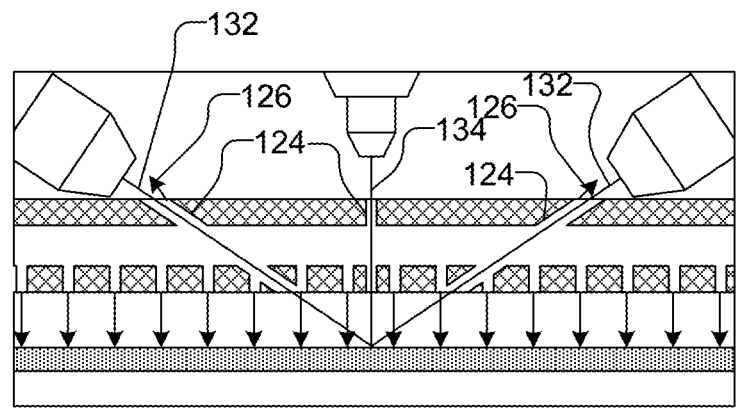
FIGS. 3 and 4 illustrate cross-sectional views of a portion of the purge gas distribution manifold showing different embodiments of ports.
Figure 4:
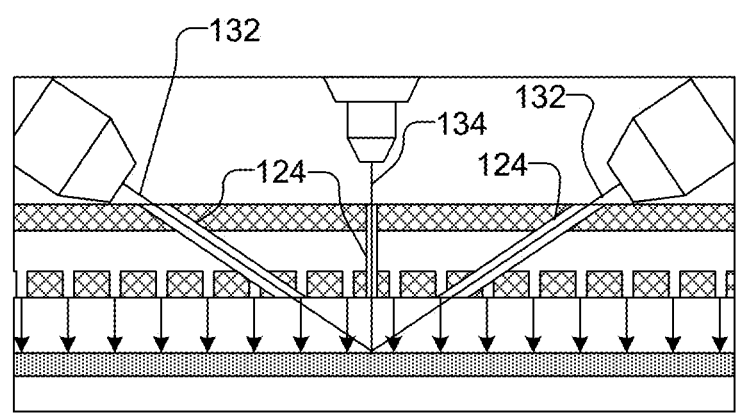

The port(s) 124 in the purge gas distribution manifold 110 may be, e.g., apertures passing through the purge gas distribution manifold 110. For example, as illustrated in a closer view of the ports 124 in FIG. 3, the ports 124 may pass through and may be fluidically coupled to the distribution plenum 114 and, thus, purge gas may be expelled through the port(s) 124 as illustrated by arrows 126. In another implementation, as illustrated in a closer view of the ports 124 in FIG. 4, the ports 124 may not be fluidically coupled to the distribution plenum 114.

The substrate 102 is held by a chuck 106 that may be coupled to a stage 108. Additionally, or alternatively, the optical metrology or inspection head 130 may be coupled to a stage (not shown). The stage 108 (and/or the stage coupled to the optical metrology or inspection head 130, produces relative motion between the chuck 106 (with substrate 102) and the optical metrology or inspection head 130 so that at least one of the chuck 106 and the optical metrology or inspection head 130 is movable to position the substrate 102 at a plurality of measurement positions with respect to the optical metrology or inspection head 130. For example, the stage 108 may move the substrate 102 linearly, e.g., within the Cartesian coordinate plane (X,Y) directions, or may rotate and linearly move the substrate 102, e.g., in Polar coordinate plane (R, θ). If desired, the substrate 102 and the optical metrology or inspection head 130 may both be moved, e.g., the substrate 102 may rotate while the optical metrology or inspection head 130 moves linearly. Alternatively, the optical metrology or inspection head 130 may move while the substrate 102 is held stationary. In implementations where the optical metrology or inspection head 130 moves linearly, it should be understood that the purge gas distribution manifold 110 may move with the optical metrology or inspection head 130.

As illustrated in FIG. 1, the bottom surface 118 of the purge gas distribution manifold 110 may be significantly larger than the substrate 102. The plurality of apertures 120 are distributed over a surface area that is larger than the surface area of a top surface of the substrate in order to distribute the purge gas over an entirety of the top surface of the substrate at all measurement positions of the substrate with respect to the optical metrology or inspection head. In one implementation, e.g., where Cartesian coordinate are used as illustrated by FIG. 2A, diameter of the purge gas distribution manifold 110 may be twice that of the substrate 102 or more, e.g., the plurality of apertures 120 may be distributed over a surface area that is at least four times the surface area of the substrate 102. In an implementation in which Polar coordinates are used as illustrated by FIG. 2B, the size of the purge gas distribution manifold 110 may be reduced so that the plurality of apertures 120 may be distributed over a surface area that is approximately 2.3 times the surface area of the substrate 102. Accordingly, as the relative motion between the substrate 102 and the optical metrology or inspection head 130 to place the substrate 102 in different measurement positions with respect to the optical metrology or inspection head 130, the entirety of the substrate 102 remains under the distribution of apertures 120 in the purge gas distribution manifold 110 at all measurement positions of the substrate 102. Thus, the purge gas distribution manifold 110 uniformly distributes the purge gas over the entire top surface 104 of the substrate 102 at all measurement positions resulting in an effective coverage protecting the top surface 104 of the substrate 102 from environmental chemical, humidity, or particle contaminants, with minimal flow of the purge gas.

Additionally, as illustrated in FIG. 1, a reference chip 140 may be coupled to the stage 108. The reference chip 140 may be, e.g., a bare silicon chip, or other appropriate chip that may be used to calibrate the optical metrology or inspection device. As optical metrology or inspection device may be sensitive to any changes in the optical properties of the reference chip 140, the purge gas distribution manifold 110 may be used to additionally provide purge gas to the reference chip 140. If desired, however, a separate purge system may be used with the reference chip 140.

The substrate 102 may be loaded onto the chuck 106, e.g., by lowering the chuck 106 to allow an end effector to place the substrate 102 on pins in the chuck 106, and the chuck 106 may then be raised to a desired height to hold the substrate 102 on the chuck surface. Alternatively, the purge gas distribution manifold 110 may have a step with greater clearance at the location where the substrate 102 is loaded onto the chuck, where the step has sufficient height to allow the end effector to place the substrate 102 on the chuck 106. With the presence of a step in a portion of the purge gas distribution manifold 110, an increased flow rate may be used in the location of the step in order to maintain purge purity.

Figure 5:
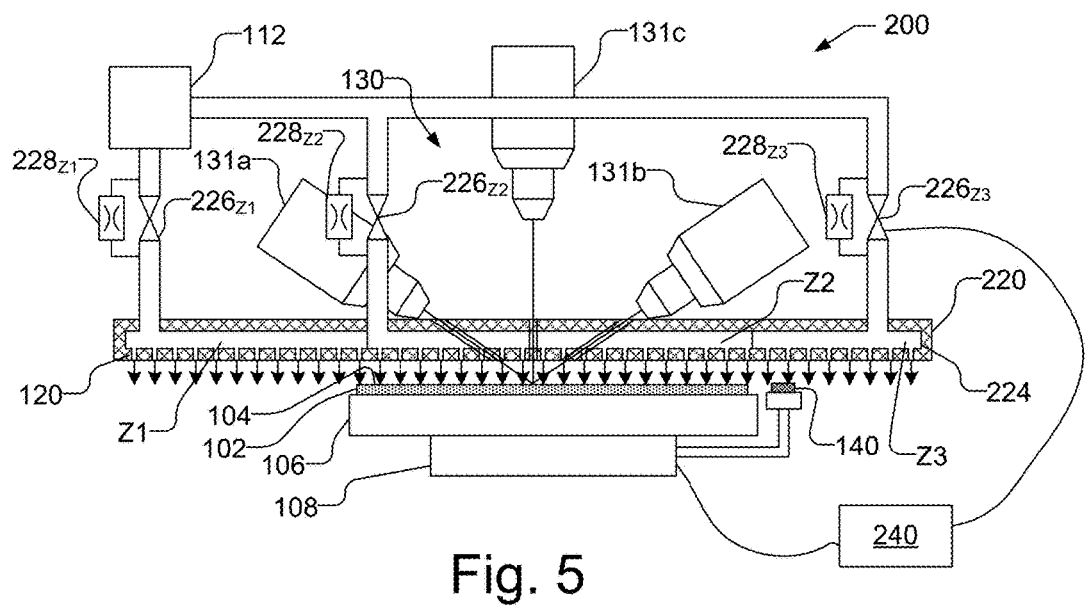
FIG. 5 illustrates a side view of a purge system with a purge gas distribution manifold that includes a plurality of zones and provides a localized clean environment for the top side of a substrate with a reduced purge gas flow.

In one implementation, the purge gas distribution manifold may be partitioned into a plurality of zones, where the flow of purge gas is switched on or off at different zones depending on whether the substrate is present or absent from each zone when the substrate is moved to different measurement positions. FIG. 5, by way of example, illustrates a side view of a purge system 200 that includes a plurality of zones to provide a localized clean environment for the top side of a substrate 102 when the substrate 102 is present within any zone, while the remaining zones have a reduced flow of purge gas. Purge system 200 is similar to purge system 100 shown in FIG. 1, like designated elements being the same. Purge system 200 includes a purge gas distribution manifold 220 that is positioned, e.g., 25 mm or less, from the top surface 104 of the substrate 102. The purge gas distribution manifold 220 includes a distribution plenum 224 that includes multiple zones Z1, Z2, Z3, each of which is fluidically coupled to a purge gas source 112 through valves $226_{Z1}$, $226_{Z2}$, $226_{Z3}$ (sometimes collectively referred to as valves 226) that independently control the flow of purge gas to their associated zones. Each valve 226 may be controlled to reduce or stop the flow of purge gas to an associated zone, for example, when the substrate 102 is not present under an associated zone. Additionally, associated with each valve $226_{Z1}$, $226_{Z2}$, $226_{Z3}$ is a bypass valve $228_{Z1}$, $228_{Z2}$, $228_{Z3}$ (sometimes collectively referred to as bypass valves 228). Each bypass valve 228 provides a reduced flow of purge gas to the associated zones in the distribution plenum 224 to maintain a charge of purge gas within the associated zone of the distribution plenum 224 when the valve to the associated zone is turned off. If a reference chip 140 is included, the valves 226 and bypass valves 228 may be controlled to provide purge gas to any zone in which the reference chip is present.

The valves 226 and bypass valves 228 may be controlled by controller 240, e.g., based on the known position of the stage 108. The controller 240 may be, e.g., a processor that controls movement of the stage 108, and thus, the substrate 102 to its different measurement positions. In another implementation, the valves 226 and bypass valves 228 may be controlled based on sensors, e.g., light sensors (not shown), that detect the presence of the substrate 102 within each zone. For some applications, the flow rate may be controlled via a software recipe control or by setting a lower flow rate passively.

Figure 6:
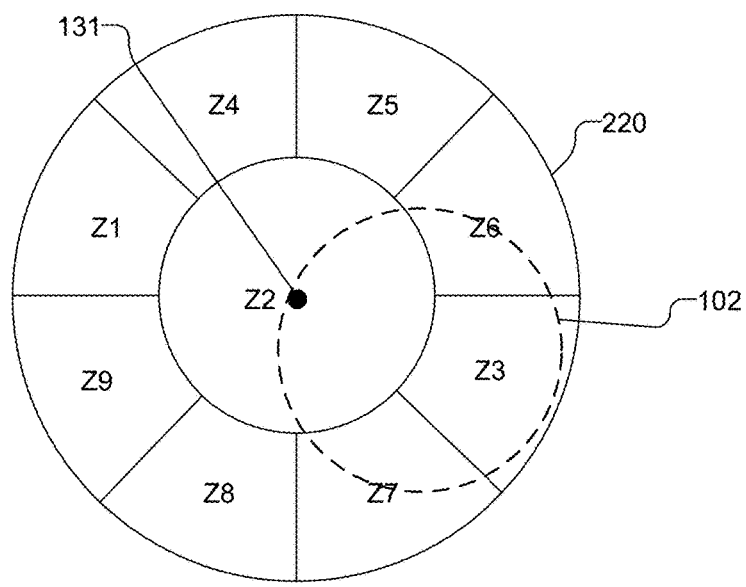
FIG. 6 is a plan view of a plurality of zones of the purge gas distribution manifold and the substrate located at a measurement position.

FIG. 6 is a plan view of the purge gas distribution manifold 220 illustrating a plurality of zones Z1, Z2, Z3, Z4, Z5, Z6, Z7, Z8, and Z9. The substrate 102 is illustrated in FIG. 6 with dotted lines at a measurement position. The optical metrology or inspection head 130 is not illustrated in FIG. 6, but the location that measurements are performed by the optical metrology or inspection head 130 is illustrated at the center of the purge gas distribution manifold 220 and is illustrated with spot 131. The substrate 102 is positioned for a measurement at the outer diameter of the substrate 102. As can be seen, the substrate 102 is present only in zones Z2, Z3, Z6 and Z7. Accordingly, valves 226 associated with zones Z2, Z3, Z6 and Z7 are controlled to produce a flow of purge gas. The valves 226 at the remaining zones, i.e., zones Z1, Z4, Z5, Z8, and Z9 may be controlled to reduce or stop the flow of purge gas. The bypass valves 228 at the remaining zones, i.e., zones Z1, Z4, Z5, Z8, and Z9, may be controlled to provide a minimum flow rate to keep gas purity high in the distribution plenum 224.

It should be understood that while FIGS. 5 and 6 illustrate three and nine zones, respectively, of the purge gas distribution manifold 220, additional or fewer zones may be used to minimize the amount of purge gas used, while maintaining an effective coverage protecting the substrate 102.

Figure 7:
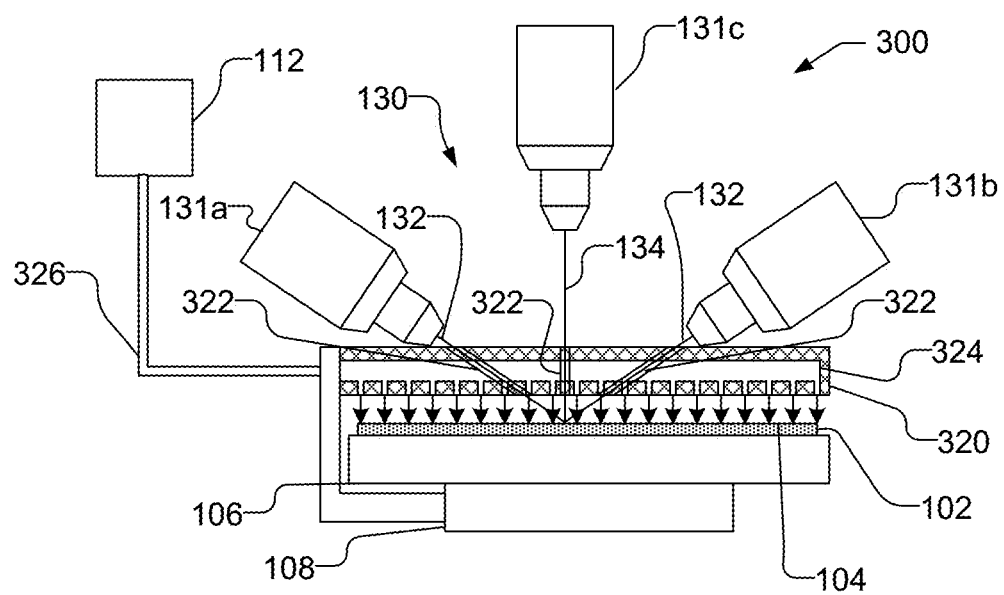
FIG. 7 illustrates a side view of a purge system that moves with the substrate to different measurement positions.

FIG. 7 illustrates a side view of another purge system 300 that is similar to purge system 100 shown in FIG. 1, like designated elements being the same. The purge system 300 includes a purge gas distribution manifold 320 that is approximately the same size as the substrate 102 and moves linearly with the substrate 102 so that the purge gas distribution manifold 320 is stationary relative to the substrate 102 for all linear movement of the substrate 102, i.e., the purge gas distribution manifold 320 is linearly stationary with respect to the substrate 102, but there may be relative rotational movement between the substrate 102 and the purge gas distribution manifold 320, e.g., as in a Polar coordinate (R, θ) movement. As illustrated in FIG. 7, the purge gas distribution manifold 320 includes a distribution plenum 324 that is fluidically coupled to a purge gas source 112 by a flexible connector 326. The purge gas distribution manifold 320 may be coupled to the chuck 106 through the stage 108 so that the purge gas distribution manifold 320 is held linearly stationary with respect to the substrate 102 when at least one of the chuck and the optical metrology or inspection head is moved to position the substrate at the plurality of measurement positions with respect to the optical metrology or inspection head. If desired, the substrate 102 may rotate with respect to the purge gas distribution manifold 320, e.g., when Polar coordinate motion is used. The flexible connector 326 may be routed through the connection between the stage 108 and the purge gas distribution manifold 320.

It should be understood that the optical metrology or inspection head 130 may move in addition to or instead of the substrate 102, but the purge gas distribution manifold 320 will remain stationary with respect to the substrate 102 for all linear movement. For example, as discussed above, the substrate 102 and the optical metrology or inspection head 130 may both be moved, e.g., the substrate 102 may rotate while the optical metrology or inspection head 130 moves linearly. Alternatively, the optical metrology or inspection head 130 may move while the substrate 102 is held stationary. The purge gas distribution manifold 320 may include elongated ports (or slots) or additional ports to accommodate movement of the optical metrology or inspection head 130 or substrate 102 to different measurement positions.

With the purge gas distribution manifold 320 held stationary with respect to the substrate 102 for all linear movement, the purge gas distribution manifold 320 does not need to be larger than the substrate 102 to cover the entire top surface 104 at all measurement positions of the substrate 102. The purge gas distribution manifold 320 may be approximately the same size as the substrate 102 to achieve the desired localized purged environment. If desired, the purge gas distribution manifold 320 may be slightly smaller than the substrate 102 and an adequate localized purged environment over the substrate 102 may be maintained for all measurement positions.

Figure 8:
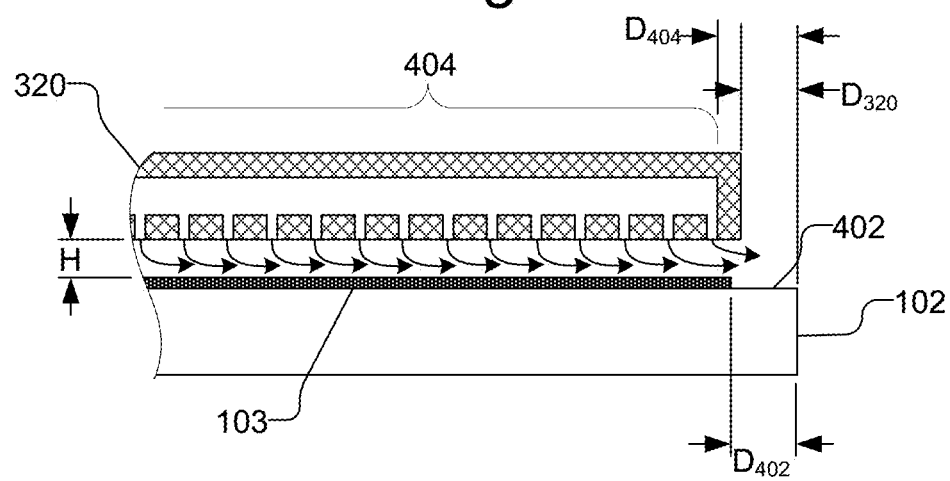
FIG. 8 illustrates a side view of portions of the purge gas distribution manifold and the substrate.

FIG. 8, by way of example, illustrates a side view of portions of the purge gas distribution manifold 320 and the substrate 102 and illustrates a possible size relationship between the purge gas distribution manifold 320 and the substrate 102. As illustrated in FIG. 8, the purge gas distribution manifold 320 is positioned a height H above the top surface of the substrate 102, which may be, e.g., 25 mm or less. The closer the purge gas distribution manifold 320 is to the substrate 102, i.e., a smaller height H, the smaller the purge gas distribution manifold 320 may be relative to the substrate 102 and less purge gas will be required to produce a desired localized purge environment over the entire surface of the substrate 102. With use of a small height H, however, loading the substrate 102 onto the chuck may require additional actions, such as lowering and raising the chuck to accommodate an end effector, which will increase the time that the substrate 102 is not within the localized purged environment and is exposed to the atmosphere.

As illustrated in FIG. 8, the substrate 102 may include an edge exclusion zone 402, which may be a distance $D_{402}$, typically 2 mm, between the edge of the substrate 102 and the area 103 on the substrate where dies are fabricated. Thus, it should be clear that the purge gas distribution manifold 320 need not extend to the edge of the substrate 102 in order to provide an adequate localized purged environment over the usable area of the substrate 102. As illustrated, the end of the purge gas distribution manifold 320 may, but is not necessarily required to, extend past the usable area of the substrate 102, i.e., over the edge exclusion zone 402. Thus, the end of the purge gas distribution manifold 320 may be a distance $D_{320}$ from the edge of the substrate 102, which for a 300 mm substrate may be 0 mm or up to 5 mm, e.g., specifically may be 2 mm (i.e., to the edge exclusion zone 402). Thus, the purge gas distribution manifold 320 may be the same size as the substrate 102 or may have a diameter that is up to 10 mm, or may be approximately 10%, smaller than the substrate 102. It should be understood that, if desired, the purge gas distribution manifold 320 may be larger than the substrate 102, but this may utilize more purge gas.

Additionally, as illustrated in FIG. 8, the purge gas distribution manifold 320 includes a surface area 404 over which the plurality of apertures are distributed, which may be smaller than the usable area of the substrate 102, i.e., the distribution area 404 of the apertures may not extend over the edge exclusion zone 402. As illustrated, the distribution area 404 of the apertures may be a distance $D_{404}$ from the edge of the substrate 102, which for a 300 mm substrate may be from 0 mm to 10 mm or from 0 mm to 20 mm. Thus, the distribution area 404 of the apertures may be the same size as the substrate 102 or may have a diameter that is up to 40 mm, or approximately 25%, smaller than the substrate 102. Moreover, with sufficiently small clearance between the purge gas distribution manifold 320 and the substrate 102, i.e., height H, it may be possible for the distribution area 404 of the apertures to be approximately 50% smaller than the substrate 102, while still providing an adequate localized purged environment to the entire surface of the substrate in all measurement positions. For example, some applications may benefit even from modest improvements in dryness, Airborne Molecular Contamination (AMC) cleanliness or O2 reduction. It should be understood that, if desired, the distribution area 404 of the apertures of the purge gas distribution manifold 320 may be larger than the substrate 102, but this may utilize more purge gas.

Figure 9:
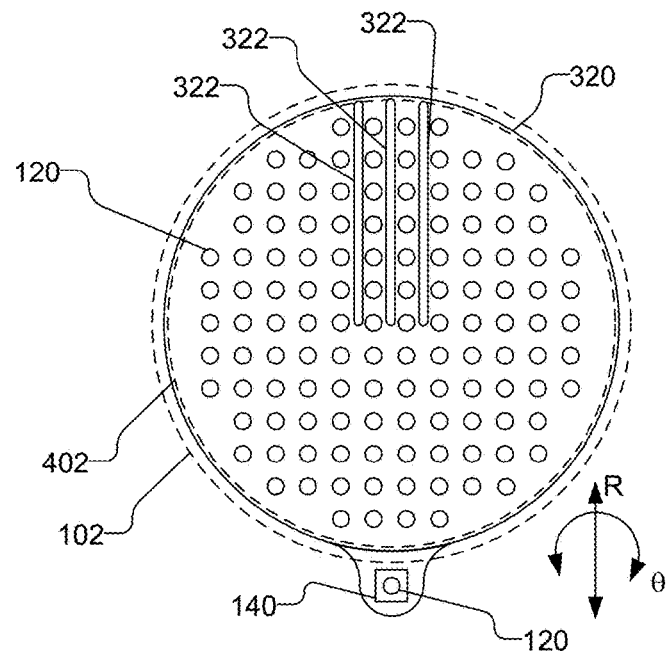
FIG. 9 illustrates a plan view of a purge gas distribution manifold that is approximately the same size as the substrate.

FIG. 9 illustrates a top plan view of purge gas distribution manifold 320 and a substrate 102 and its edge exclusion zone 402 shown with broken lines. As illustrated, the purge gas distribution manifold 320 may include one or more linear ports 322 or slots that are the length of a full radius of the substrate 102, which permits the light beams, such as obliquely incident light beam 132 and normally incident light beam 134, to access the substrate 102. The purge gas distribution manifold 320 and a substrate 102 are held linearly stationary with respect to each other, so that as the substrate 102 is moved linearly to different measurement positions, or alternatively, as the optical metrology or inspection head 130 is moved linearly with respect to the substrate 102 and the purge gas distribution manifold 320, the purge gas distribution manifold 320 remains stationary with respect to the substrate 102 and, accordingly, will continue to provide a localized purge environment to the entire surface of the substrate 102 at all measurement positions. Moreover, because the size of the purge gas distribution manifold 320 is much reduced compared to the purge gas distribution manifold 110 shown in FIG. 1, less purge gas is required by the purge gas distribution manifold 320.

Additionally, as illustrated in FIG. 9, the reference chip 140 may be used with the purge system 300 where, for example, the purge gas distribution manifold 320 is extended to cover the reference chip 140. If desired, one or more purge apertures 120 in the purge gas distribution manifold 320 may be located over the reference chip 140.

Figure 10A:
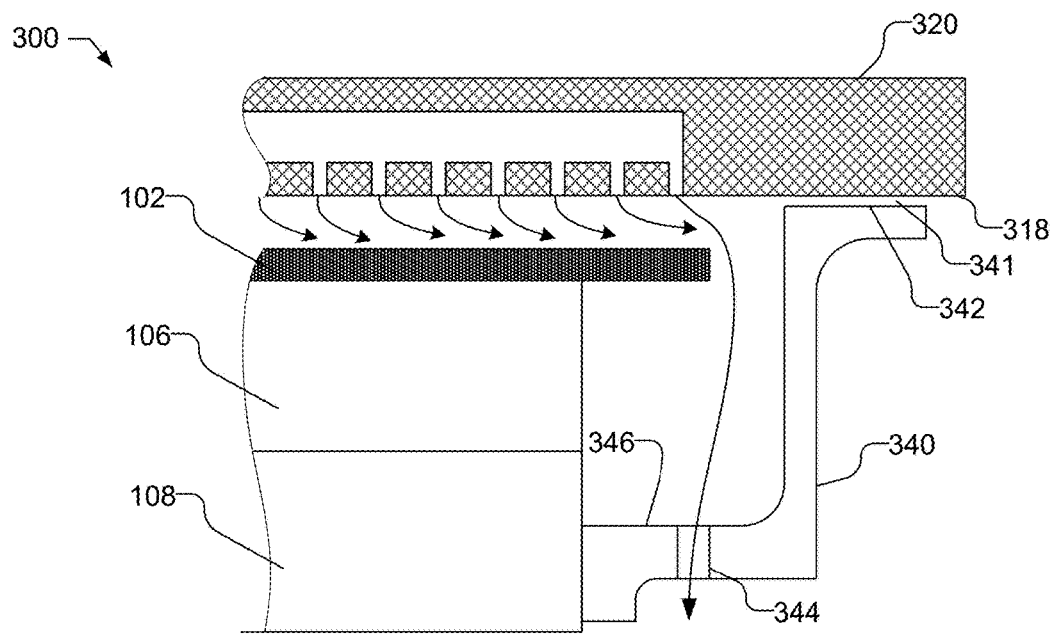
FIGS. 10A and 10B illustrate side views of a portion of a purge gas distribution manifold and a portion of a fence that surrounds a substrate.

If desired, additional components may be included with the purge system 300, which may assist in providing a localized purge environment while minimizing the purge gas flow rate. For example, a fence may surround the substrate 102 to contain and direct the purge gas. FIG. 10A, by way of example, illustrates a side view of a portion of a fence 340 that surrounds the substrate 102. If a reference chip is present (not shown in FIG. 10A), both the substrate 102 and the reference chip may be surrounded by the fence 340. The fence 340 may have a fixed height and may be coupled to the stage 108 so that the fence 340 moves linearly with the chuck 106 and substrate 102. As with the purge gas distribution manifold 320, if desired, the chuck 106 and substrate 102 may be permitted to rotate with respect to the fence 340. During substrate load and unload, the fence 340 may move downward with the stage 108 to allow an end effector to place the substrate 102 on or remove the substrate 102 from pins in the chuck 106, and the chuck 106 may then be raised to a desired height. If desired, the fence 340 may move independently of the Z stage.

The fence 340 may include an upper surface 342 that is positioned near the bottom surface 318 of the purge gas distribution manifold 320. For example, the vertical gap 341 between the upper surface 342 of the fence 340 and the bottom surface 318 of the purge gas distribution manifold 320 may be 10 mm or less. The fence 340 may include one or more, e.g., 1 to 150, apertures 344, which may be, e.g., up to 25 mm in diameter, through which the purge gas may be exhausted passively or actively, e.g., using a pump. By way of example, the apertures 344 may be located below the top surface of the substrate 102, such as on a bottom surface 346 of the fence 340.

Figure 10B:
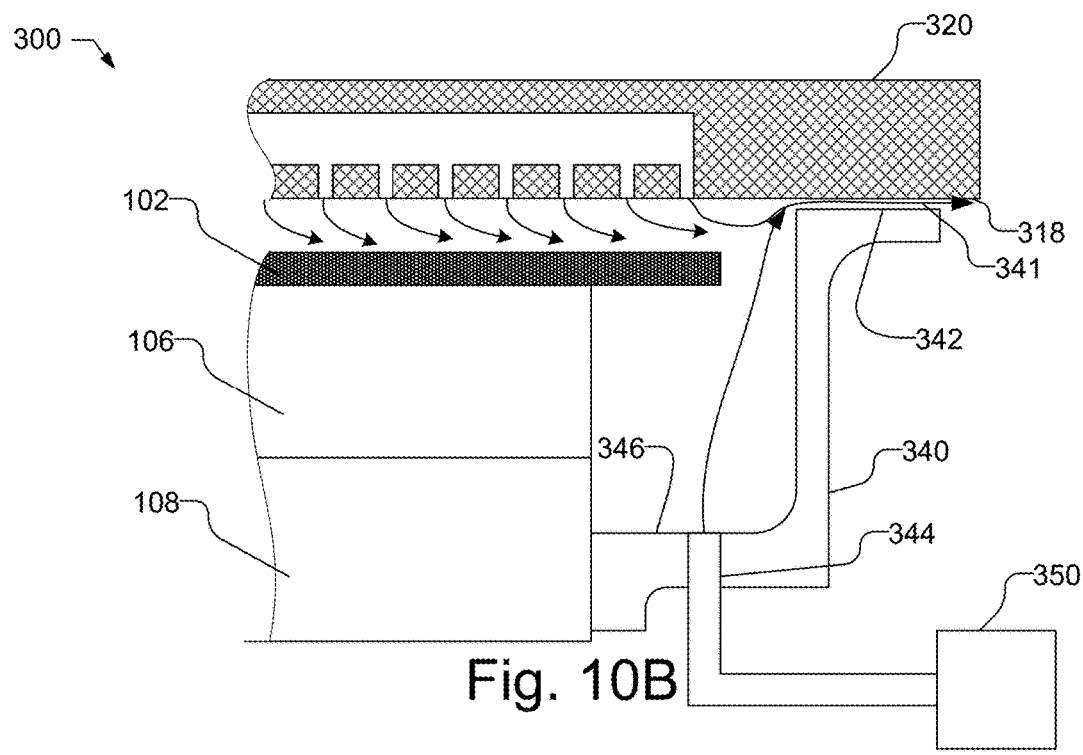

FIG. 10B illustrates a portion of a side view of another implementation of the fence 340 that surrounds the substrate 102. As illustrated in FIG. 10B, the apertures 344 may be fluidically coupled to a purge gas source 350 (which may be the same or a different purge gas source that is fluidically coupled to the purge gas distribution manifold 320. Purge gas may be emitted by the one or more apertures 344, which may be located below the top surface of the substrate 102, e.g., on the bottom surface 346 of the fence 340. Alternatively, the fence 340 may not include apertures 344. The purge gas that is emitted by the purge gas distribution manifold 320 may not be exhausted through apertures in the bottom surface 346 of the fence 340, but rather through the vertical gap 341 between the upper surface 342 of the fence 340 and the bottom surface 318 of the purge gas distribution manifold 320, as illustrated by the arrows. Purge gas emitted by the apertures 344 in the fence 340, if used, may likewise be exhausted through the vertical gap 341.

Figure 11:
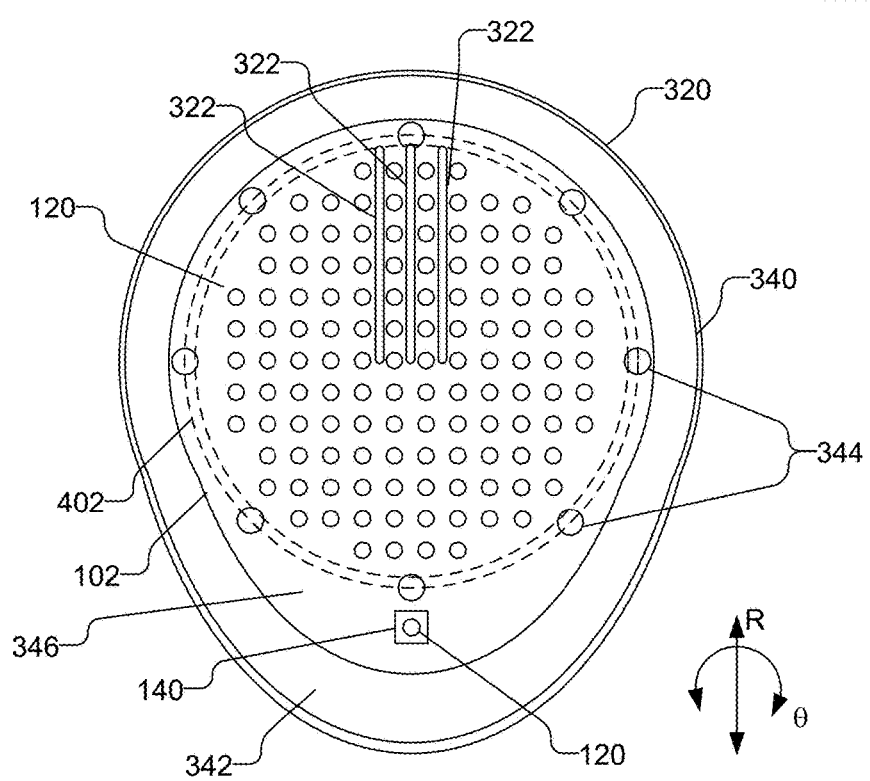
FIG. 11 illustrates a plan view of a purge gas distribution manifold and a fence that surrounds a substrate and reference chip.

FIG. 11 illustrates a top plan view of purge gas distribution manifold 320 with the fence 340, where the substrate 102 and its edge exclusion zone 402 are shown with broken lines. FIG. 11 is similar FIG. 9, like designated elements being the same. As illustrated, fence 340 surrounds the substrate 102, as well as the reference chip 140, if used. The purge gas distribution manifold 320 may extend beyond the outside edge of the upper surface 342 of the fence 340. The apertures 344 in the bottom surface 346 of the fence 340 may be underneath the substrate 102. The fence 340, along with the purge gas distribution manifold 320 may be held linearly stationary with respect to the substrate 102, i.e., so that they are held stationary with respect to each other during linear movement, but there may be relative rotational movement. Thus, the fence 340 and purge gas distribution manifold 320 will provide a localized purge environment to the entire surface of the substrate 102 at all measurement positions.

Figure 12:
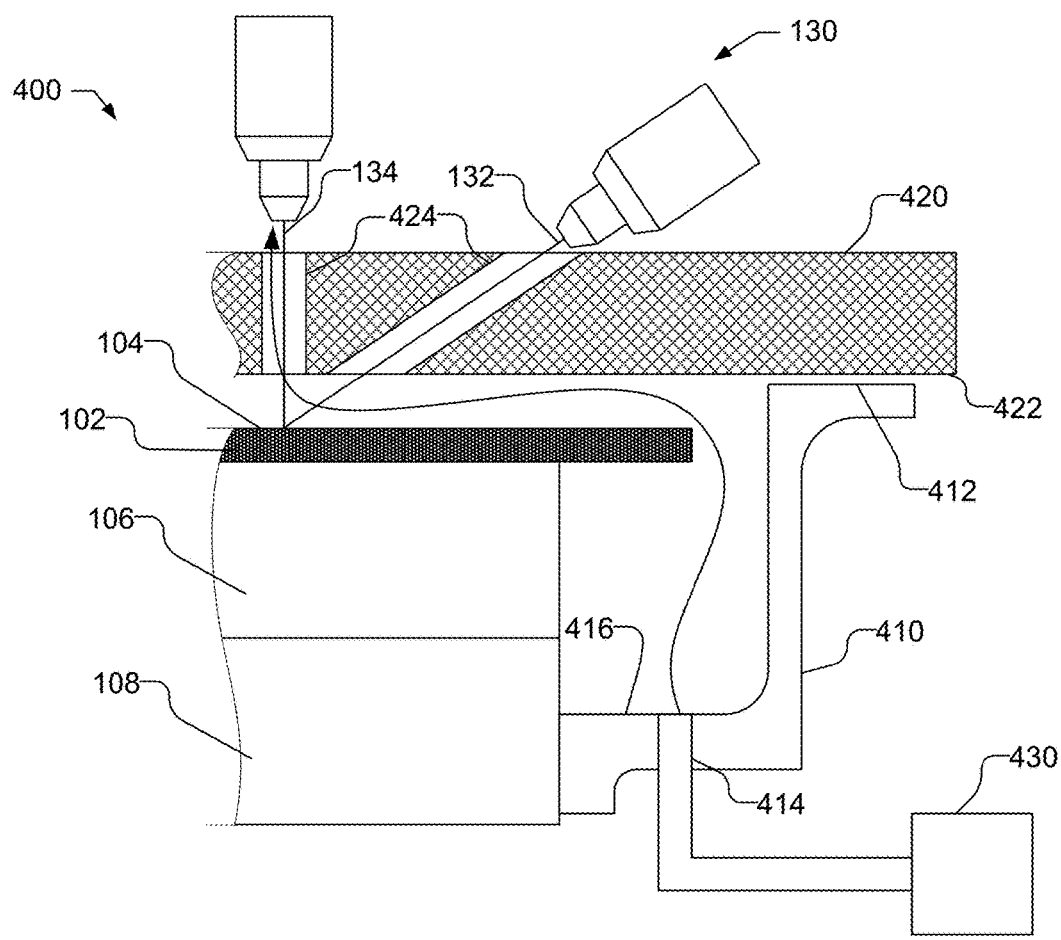
FIG. 12 illustrates a side view of a purge system in which purge gas is provided into the localized environment around the substrate through a fence.

If desired, the purge gas may be provided through the fence to produce a localized purge environment above the substrate 102. FIG. 12, by way of example, illustrates a side view of a purge system 400 in which purge gas is provided into the localized environment around the substrate 102 through a fence 410. The purge system 400 shown in FIG. 12, is similar to that shown in FIGS. 10A and 10B, like designated elements being the same. As illustrated, purge gas may be provided from a purge gas source 430 through one or more apertures 414 (e.g., 1 to 150 apertures) in the fence 410 which surrounds the substrate 102 to contain and direct the purge gas over the top surface of the substrate 102. The apertures 414 may be, e.g., up to 25 mm in diameter and may be located below the top surface of the substrate 102, e.g., on the bottom surface 416 of the fence 410. Similar to the fence shown in FIGS. 10A and 10B, the fence 410 may have a fixed height and may be coupled to the stage 108 so that the fence 410 moves linearly with the chuck 106 and substrate 102. The fence 410 may include an upper surface 412 that is positioned near the bottom surface 422 of a ceiling 420, e.g., 10 mm or less. Similar to the purge gas distribution manifold 320, the bottom surface 422 of the ceiling 420 may be positioned 25 mm or less from the top surface 104 of the substrate 102 to minimize the purge gas consumption while providing good shielding purity in the local environment over the substrate 102.

The ceiling 420 may be coupled to the stage 108 and may be linearly stationary with respect to the chuck 106, substrate 102 and fence 410, i.e., there is no relative movement between the ceiling 420 and the chuck 106, substrate 102 and fence 410 during linear motion, but relative rotational movement may be permitted. Alternatively, the ceiling 420 may be coupled to the optical metrology or inspection head 130 so that there is relative linear and rotational movement between the ceiling 420 and the chuck 106, substrate 102, and fence 410. Thus, relative movement using Cartesian coordinates or Polar coordinates is possible. The ceiling 420 may include apertures 424 (or slots) through which light beams 132 and 134 from the optical metrology or inspection head 130 may be transmitted. As illustrated by the arrow, the purge gas may be exhausted through apertures 424, or may be exhausted through other apertures (not shown) above the top surface of the substrate 102. Similar to fence 340, during substrate load and unload, the fence 410 may move downward with the stage 108 to allow an end effector to place the substrate 102 on or remove the substrate 102 from pins in the chuck 106, and the chuck 106 may then be raised to a desired height. If desired, the fence 410 may move independently of the Z stage.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. An apparatus comprising:
    an optical metrology or inspection head that produces a light beam that is incident on a substrate to be optically measured and is received by the optical metrology or inspection head after interacting with the substrate;
    a chuck for holding the substrate, wherein at least one of the chuck and the optical metrology or inspection head is movable to position the substrate at a plurality of measurement positions with respect to the optical metrology or inspection head; and
    a purge gas distribution manifold coupled to a purge gas source, the purge gas distribution manifold having at least one port through which the light beam is transmitted, the purge gas distribution manifold having a bottom surface that is 25 mm or less from a top surface of the substrate and has a plurality of apertures through which purge gas is expelled over the top surface of the substrate, wherein the plurality of apertures are distributed over a surface area that is at least as large as a surface area of the top surface of the substrate to distribute the purge gas over an entirety of the top surface of the substrate at all measurement positions of the substrate with respect to the optical metrology or inspection head.

2. The apparatus of claim 1, wherein the purge gas comprises an inert gas.

3. The apparatus of claim 2, wherein the inert gas comprises at least one of clean dry air, nitrogen, argon or a combination thereof.

4. The apparatus of claim 1, wherein the plurality of apertures in the bottom surface of the purge gas distribution manifold is formed by a porous media.

5. The apparatus of claim 1, wherein the plurality of apertures in the bottom surface of the purge gas distribution manifold is a pattern of holes.

6. The apparatus of claim 5, wherein the holes are coupled to distribution grooves.

7. The apparatus of claim 1, wherein the purge gas distribution manifold is partitioned into a plurality of zones, the purge gas distribution manifold further comprises a plurality of valves coupled to the purge gas source, wherein each zone is associated with at least one valve, each valve being controlled to reduce or stop a flow of purge gas to an associated zone when the substrate is not present within the associated zone.

8. The apparatus of claim 7, further comprising a plurality of bypass valves associated with each valve, wherein each bypass valve provides a reduced flow of purge gas to maintain a charge of purge gas within an associated zone when an associated valve is shut off.

9. The apparatus of claim 1, wherein the purge gas distribution manifold is held linearly stationary with respect to the substrate when the at least one of the chuck and the optical metrology or inspection head is moved to position the substrate at the plurality of measurement positions with respect to the optical metrology or inspection head.

10. The apparatus of claim 1, further comprising a fence surrounding the substrate on the chuck, wherein the fence is held linearly stationary with respect to the substrate when the at least one of the chuck and the optical metrology or inspection head is moved to position the substrate at the plurality of measurement positions with respect to the optical metrology or inspection head.

11. The apparatus of claim 10, wherein the fence comprises an upper surface that is 10 mm or less from the bottom surface of the purge gas distribution manifold.

12. The apparatus of claim 1, further comprising a reference chip, wherein the purge gas distribution manifold extends over the reference chip.

* * * * *